United States Patent [19]

Varma

[11] Patent Number: 4,529,547
[45] Date of Patent: Jul. 16, 1985

[54] 17-(SUBSTITUTED THIO)-17-(SUBSTITUTED DITHIO) ANDROSTENES

[75] Inventor: Ravi K. Varma, Belle Mead, N.J.

[73] Assignee: E.R. Squibb & Sons, Inc., Princeton, N.J.

[21] Appl. No.: 622,508

[22] Filed: Jun. 20, 1984

[51] Int. Cl.³ .................................................. C07J 1/00
[52] U.S. Cl. ............................ 260/397.3; 260/397.45
[58] Field of Search .............. 260/397.45, 397.5, 397.3

[56] References Cited

U.S. PATENT DOCUMENTS

| | | | |
|---|---|---|---|
| 4,091,036 | 5/1978 | Varma | 260/397.45 |
| 4,094,840 | 6/1978 | Varma | 260/397.45 |
| 4,133,811 | 1/1979 | Varma | 260/397.45 |
| 4,146,538 | 3/1979 | Varma et al. | 260/397.45 |
| 4,361,559 | 11/1982 | Varma | 260/397.45 |
| 4,427,592 | 1/1984 | Varma et al. | 260/397.45 |
| 4,435,326 | 3/1984 | Varma | 260/397.45 |
| 4,447,426 | 5/1984 | Wang et al. | 260/397.45 |

*Primary Examiner*—Elbert L. Roberts
*Attorney, Agent, or Firm*—Lawrence S. Levinson; Donald J. Barrack

[57] ABSTRACT

Topical antiinflammatory activity is by steroids having the formula

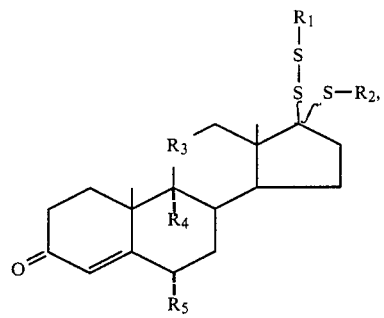

and the 1,2-dehydro derivatives thereof wherein
$R_1$ and $R_2$ are the same or different and each is alkyl, aryl, arylalkyl or cycloalkyl;
$R_3$ is carbonyl or $\beta$-hydroxymethylene;
$R_4$ is hydrogen or halogen; and
$R_5$ is hydrogen, methyl or fluorine.

10 Claims, No Drawings

17-(SUBSTITUTED THIO)-17-(SUBSTITUTED DITHIO) ANDROSTENES

BACKGROUND OF THE INVENTION

U.S. Pat. Nos. 4,091,036, issued May 23, 1978, 4,094,840, issued June 13, 1978, 4,133,811, issued Jan. 9, 1979, and 4,146,538, issued Mar. 27, 1979, each discloses androstene intermediates having the partial structural formula

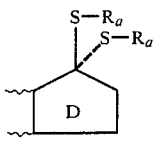

wherein $R_a$ is alkyl or aryl, and both $R_a$ groups are the same.

U.S. Pat. No. 4,361,559, issued Nov. 30, 1982, discloses androstene-17-dithioketals having the partial structural formula

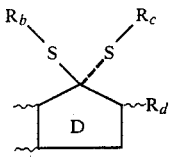

wherein $R_b$ and $R_c$ are the same or different and each is alkyl, cycloalkyl, or aryl; $R_d$ is hydrogen, hydroxy, alkoxy, aryloxy, alkylthio, arylthio,

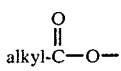

or halogen; and the broken line in the 15,16-position represents the optional presence of ethylenic unsaturation. The steroids have antiinflammatory activity.

U.S. Pat. No. 4,447,426, issued May 8, 1984, discloses androstene-17-dithioketals having the partial structural formula

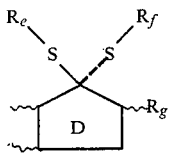

wherein one of $R_e$ and $R_f$ is alkyl, cycloalkyl, aryl, arylalkyl or —CH$_2$X wherein X is alkylthio, alkoxy, aroyloxy, alkanoyloxy or alkoxycarbonyl and the other is alkylthioalkyl, alkoxyalkyl, alkanoyloxyalkyl, aroyloxyalkyl, alkoxycarbonylalkyl, carboxylalkyl or arylalkyl; $R_g$ is hydrogen, hydroxy, alkoxy, aryloxy, oxo, methylene, alkylthio, arylthio, alkanoyl, alkanoyloxy, or halogen; and the broken line in the 15,16-position represents the optional presence of ethylenic unsaturation. The steroids have antiinflammatory activity.

U.S. Pat. No. 4,435,326, issued Mar. 6, 1984, discloses androstene-17-dithioketals having the partial structural formula

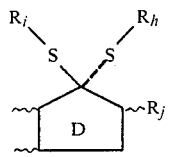

wherein $R_h$ is hydrogen and $R_i$ is alkyl, cycloalkyl, aryl, arylalkyl, alkylthioalkyl, alkoxyalkyl, alkanoyloxyalkyl, aroyloxyalkyl, alkoxycarbonylalkyl, carboxyalkyl, or arylalkyl, or $R_h$ is alkanoyl or aroyl and $R_i$ is alkyl; and $R_j$ is hydrogen, hydroxy, alkoxy, aryloxy, oxo, methylene, alkylthio, aryltiho, alkanoyl, alkanoyloxy, or halogen. The steroids are useful intermediates for preparing steroids with antiinflammatory activity.

U.S. Pat. No. 4,427,592, issued Jan. 24, 1984, discloses androstene-17-dithioketals having the partial structural formula

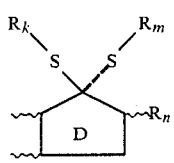

wherein one of $R_k$ and $R_m$ is alkyl, aryl, arylalkyl, or cycloalkyl, and the other is alkenyl, substituted alkenyl, alkynyl, substituted alkynyl, mono-, di- or trifluoroalkyl, cyanoalkyl, alkanoylalkyl or

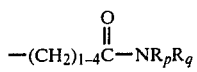

wherein $R_p$ and $R_q$ are the same or different and each is hydrogen or alkyl.

BRIEF DESCRIPTION OF THE INVENTION

Steroids having the formula

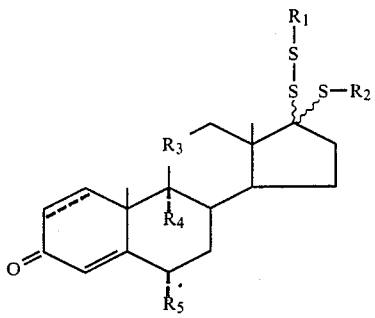

have topical antiinflammatory activity. In formula I, and throughout the specification, the symbols are as defined below.

$R_1$ and $R_2$ are the same or different and each is alkyl, aryl, arylalkyl or cycloalkyl;

$R_3$ is carbonyl or β-hydroxymethylene;

$R_4$ is hydrogen or halogen; and $R_5$ is hydrogen, methyl or fluorine.

A broken line in the 1,2-position of a structural formula in this specification indicates the optional presence of ethylenic unsaturation.

The term "aryl", as used throughout the specification either individually or as part of a larger group, refers to phenyl or phenyl substituted with one or two alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or part of a larger group, refer to groups having 1 to 12 carbon atoms.

The term "cycloalkyl" as used throughout the specification, either individually or as part of a larger group, refer to groups having 3, 4, 5, 6 or 7 carbon atoms.

DETAILED DESCRIPTION OF THE INVENTION

The steroids of formula I are topical antiinflammatory agents that can be used to treat skin conditions such as dermatitis, psoriasis, sunburn, eczema, neurodermatitis, or anogenital pruritus, and in inhalation therapy for topical treatment of allergy and asthma.

For the treatment of skin conditions, the topical antiinflammatory steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma, the topical antiinflammatory steroids of this invention may be administered in the conventional manner, e.g., as solid medicament which has been atomized. U.S. Pat. Nos. 3,948,264 and 4,147,166 are exemplary of the literature which describes devices that can be used to administer solid medicaments for inhalation therapy.

The androstenes of this invention can be prepared from the corresponding androstene having the formula

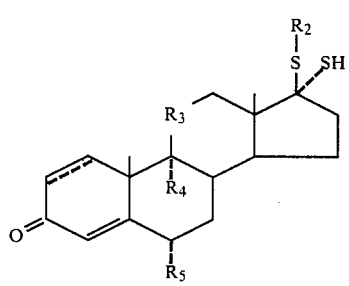

II

Androstenes of formula II are known; see, for example, U.S. Pat. No. 4,446,071, issued May 1, 1984.

To prepare those androstenes of formula I wherein the 17-substituted dithio substituent is in the alpha configuration, a steroid of formula II is reacted with a compound having the formula $R_1-S-SO_2-R_1$  III The reaction is preferably carried out in an organic solvent such as dimethylformamide, in the presence of an inorganic base such as sodium bicarbonate, and yields a steroid having the formula

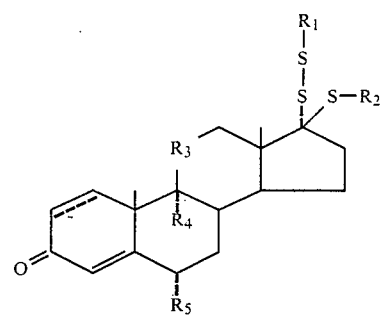

IV

To prepare those androstenes of formula I wherein the 17-substituted dithio substituent is in the beta configuration, a steroid of formula II is first reacted with a compound having the formula $R_1-SX,$  V wherein X is chlorine or bromine. The reaction is preferably carried out in an organic solvent such as dimethylformamide or dichloromethane, in the presence of an inorganic base such as sodium bicarbonate, and yields a $\Delta^{16}$-steroid having the formula

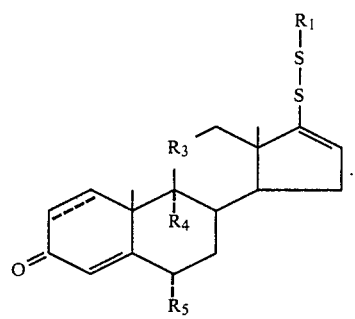

VI

Reaction of a $\Delta^{16}$-steroid of formula VI with a thiol having the formula $R_2-SH$  VII in the presence of an organic acid such as trifluoroacetic acid yields the corresponding androstene having the formula

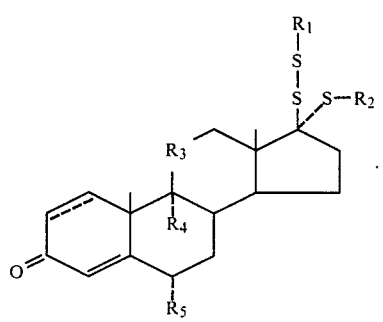

VIII

Alternatively, a $\Delta^{16}$-steroid intermediate of formula VI can be prepared by reacting a 17-thione androstene having the formula

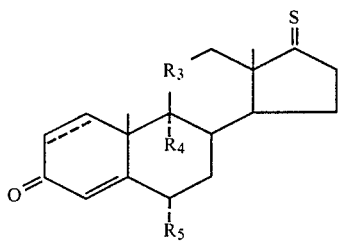

with a compound of formula III, preferably in dimethylformamide, in the presence of sodium bicarbonate. Androstenes of formula IX are known; see, for example, U.S. Pat. No. 4,427,592, issued Jan. 24, 1984.

In the above-described reactions it may be necessary (when, in the desired product, $R_3$ is $\beta$-hydroxymethylene) to protect the 11$\beta$-hydroxyl group of the steroid starting materials and intermediates. An exemplary family of protecting groups is the acyl family, e.g., alkanoyl groups such as acetyl. Means for protection and deprotection of the 11$\beta$-hydroxyl group are well known in the art.

The following examples are specific embodiments of this invention.

EXAMPLE 1

(11$\beta$,17$\alpha$)-9-Fluoro-11-hydroxy-17-(methyldithio)-17-(methylthio)androsta-1,4 dien-3-one (A)

(11$\beta$,17$\alpha$)-11-(Acetyloxy)-9-fluoro-17-(methyldithio)-17-(methylthio)androsta-1,4-dien-3-one To a stirred solution of methanethiolmethane sulfonate (0.44 mmol, 56 mg) in dry dimethylformamide (5.0 ml) was added simultaneously a mixture of dried sodium bicarbonate (2.0 mmol, 170 mg) and (11$\beta$,17$\alpha$)-11-(acetyloxy)-9-fluoro-17-(mercapto)-17-(methylthio)androsta-1,4-diene-3-one (0.4 mmol, 170 mg). A clean reaction to give a single less polar product was noticed by TLC in less than 30 minutes (silica gel, chloroform-methanol, (95:5)). The mixture was then added into water and extracted with chloroform. The chloroform solution was washed with water, dried (anhydrous magnesium sulfate) and was evaporated to give the title compound as a solid (160 mg) with a consistent NMR spectrum.

(B)

(11$\beta$,17$\alpha$)-9-Fluoro-11-hydroxy-17-(methyldithio)-17-(methylthio)androsta-1,4 dien-3-one A solution of (11$\beta$,17$\alpha$)-11-(acetyloxy)-9-fluoro-17-(methyldithio)-17-(methylthio)androsta-1,4-dien-3-one (160 mg) was stirred with 3M sodium hydroxide (0.75 ml) in a mixture of tetrahydrofuran (5.0 ml) and methanol (5.0 ml) under an atmosphere of nitrogen at room temperature for 45 minutes. A clean reaction to give a more polar compound was noticed by TLC (silica gel, chloroform-methanol (95:5)). A slight excess of acetic acid was then added and the mixture was concentrated in vacuo. The residue was diluted with water and extracted with dichloromethane. The extracts were combined, washed with water, dried (anhydrous magnesium sulfate), and evaporated to afford the title compound as a solid (130 mg). Two crystallizations of this from ethyl acetate hexane followed by drying (80° C., 0.3 mm of Hg, 18 hours) afforded the analytical specimen (50 mg), melting point 186°–187° C. with consistent spectral data.

Analysis Calc'd. for $C_{21}H_{29}FO_2S_3$: C, 58.84; H, 6.18; F, 4.43; S, 22.44. Found: C, 59.06; H, 6.22; F, 4.52, S, 22.29.

What is claimed is:

1. A steroid having the formula

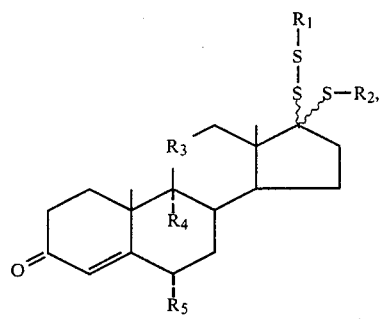

or the 1,2-dehydro derivative thereof, wherein $R_1$ and $R_2$ are the same or different and each is alkyl, aryl, arylalkyl or cycloalkyl;

$R_3$ is carbonyl or $\beta$-hydroxymethylene;

$R_4$ is hydrogen or halogen; and $R_5$ is hydrogen, methyl or fluorine.

2. A steroid in accordance with claim 1 wherein $R_3$ is $\beta$-hydroxymethylene.

3. A steroid in accordance with claim 1 wherein $R_4$ is fluorine.

4. A steroid in accordance with claim 1 wherein $R_5$ is hydrogen.

5. A steroid in accordance with claim 1 wherein $R_3$ is $\beta$-hydroxymethylene, $R_4$ is fluorine and $R_5$ is hydrogen.

6. A steroid in accordance with claim 1 wherein $R_1$ and $R_2$ are each alkyl.

7. A steroid in accordance with claim 6 wherein $R_1$ and $R_2$ are each methyl.

8. A steroid in accordance with claim 5 wherein $R_1$ and $R_2$ are each alkyl.

9. A steroid in accordance with claim 8 wherein $R_1$ and $R_2$ are each methyl.

10. The steroid in accordance with claim 1, (11$\beta$,17$\alpha$)-9-fluoro-11-hydroxy-17-(methyldithio)-17-(methylthio)androsta-1,4-dien-3-one.

* * * * *